(12) United States Patent
Komori et al.

(10) Patent No.: US 6,277,614 B1
(45) Date of Patent: Aug. 21, 2001

(54) DEOXYRIBONUCLEASE

(75) Inventors: Kayoko Komori, Suita; Yoshizumi Ishino, Takatsuki, both of (JP)

(73) Assignee: Biomolecular Engineering Research Institute, Osaka (JP)

( * ) Notice: Subject to any disclaimer, the term of this patent is extended or adjusted under 35 U.S.C. 154(b) by 0 days.

(21) Appl. No.: 09/448,280

(22) Filed: Nov. 24, 1999

(30) Foreign Application Priority Data

Nov. 25, 1998 (JP) .................................................. 10-333925

(51) Int. Cl.$^7$ ....................................................... C12N 9/22
(52) U.S. Cl. ................................................................. 435/194
(58) Field of Search ............................................... 435/194

(56) References Cited

PUBLICATIONS

Komori, et al. (1999) Proc Natl. Acas. Sci., USA 96, 8873–8878.*

"Recognition and Manipulation of Branched DNA Structure by Junction–resolving Enzynes" (J. Mol. Biol (1977) 269, pp. 647–664) (White, et al.).

"Holliday Junction Processing in Bacteria: Insights from Evolutionary Conservation in RuvABC, RecG, and RusA" (Journal of Bacteriology, Sep. 1999, pp. 5543–5550) (Sharpley, et al.).

"Processing the Holliday junction in homologous recombination "(TIBS 21 Mar. 1996, pp. 107–111) (Shinagawa, et al.).

Kayoko Komori et al., "PI–Pful and PI–Pfull, intein–induced homing endonucleases from *Pyrococcus furiosus*. I. Purification and identification of the homing–type endonuclease activities", *Nucleic Acids Research*, vol. 27, No. 21, pp. 4167–4174 (1999).

Joan Riera et al., "Ribonucleotide reductase in the archaeon *Pyrococcus furiosus*: A critical enzyme in the evolution of DNA genomes?", *Proc. Natl. Acad. Sci. USA*, vol. 94, pp. 475–478 (Jan. 1997).

Steven J. Sandler et al., "recA–Like genes from three archaen species with putative protein products similar to Rad51 and Dmc1 proteins of the yeast *Saccharomyces cerevisiae*", *Nucleic Acids Research*, vol. 25, No. 11, pp. 2125–2132 (1996).

Norimichi Nomura et al., "Molecular Characterization and Postsplicing Fate of Three Introns within the Single rRNA Operon of the Hyperthermophilic Archaeon *Aeropyrum pernix*K1", *Journal of Bacteriology*, vol. 180, No. 14, pp. 3635–3643, (Jul. 1998).

Hiromi Daiyasu et al., "Hjc resolvase is a distantly related member of the type II restriction endonuclease family", *Nucleic Acids Research*, vol. 28, No. 22, pp. 4540–4543 (2000).

* cited by examiner

*Primary Examiner*—Charles L. Patterson, Jr.
(74) *Attorney, Agent, or Firm*—Wenderoth, Lind & Ponack, L.L.P.

(57) ABSTRACT

The present invention provides a thermostable protein having deoxyribonuclease activity that specifically acts on and cleaves a Holliday structured DNA, which is an intermediate structure in the DNA recombination process, to resolve it into two sets of double-stranded DNAs.

4 Claims, 10 Drawing Sheets

Four-way junction structure of which center migrates

Four-way junction structure of which center does not migrate

Three-way junction structure of which center migrates

Three-way junction structure
of which center does not migrate

FIG. 5
Loop-out structure

```
5'                                                                              3'
CGTTAAGCTAGCAACTGTAGAGCGGCAGGAGGTCTACGGCCTCACTTCAAGGTTGCAAGCCG
GCAATTCGATCGTTGACATCTCGCCGTCGTCCTCCAG    ATGCGGAGTGAAGTTCCAACGTTCGGC
                                   GG    GG
                                   CT    GC
                                    CAAT
3'                                                                              5'
```

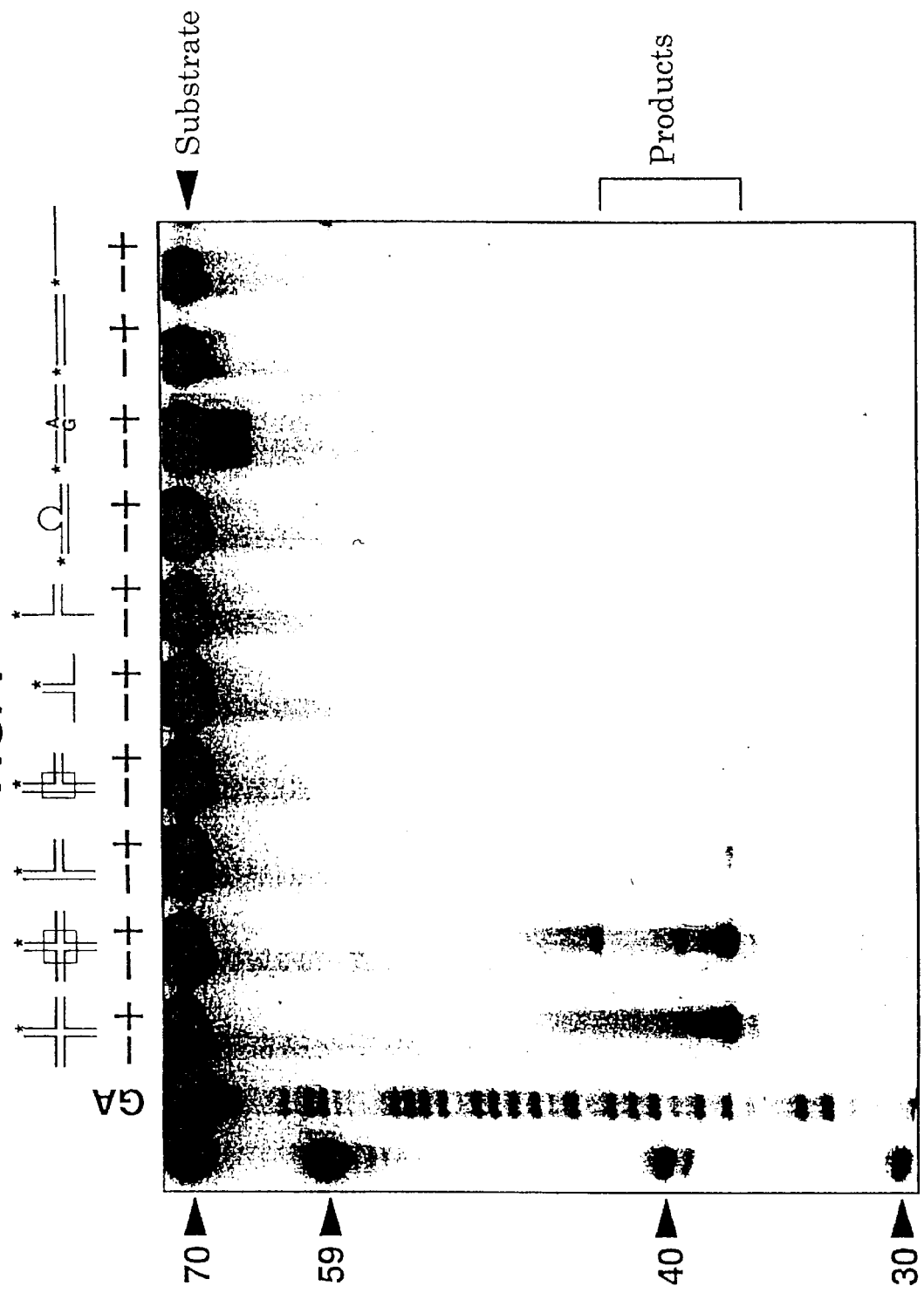

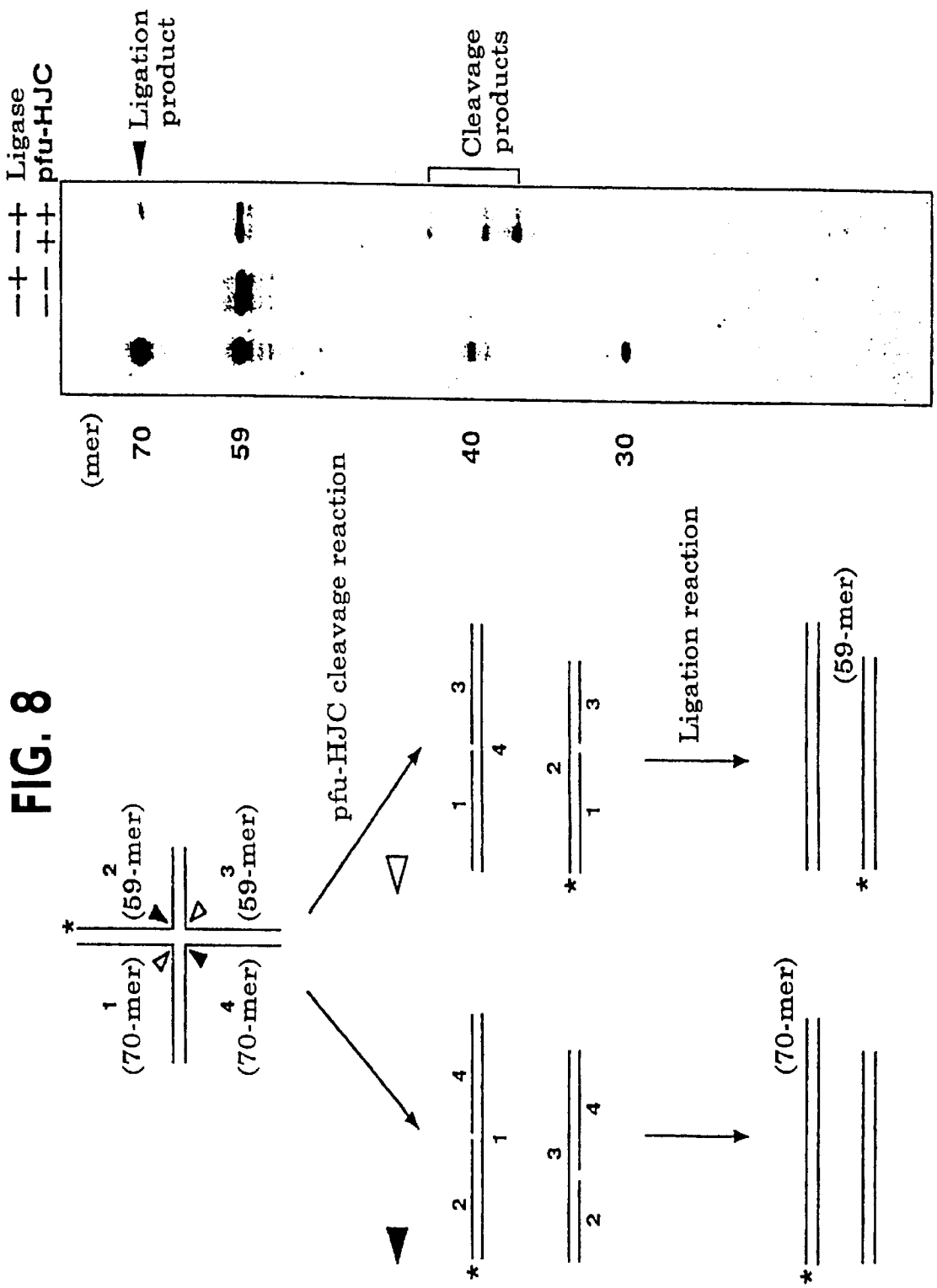

FIG. 9

Homology of amino acids

```
pfu    ---MYRKGAQAERELIKLLEKHGFAVVRSAGS------KKVDLVAGNGKKYLCIEVKVTK
pho    ---MYRKGANAERELIKKLERLGFAVIRSAGS------KKVDVVAGNGKIYLCIEVKTTK
mja    MRHKYRKGSSFERELKRLLEKEGFAVIRSAGS------KGVDLIAGRKGEVLIFECKTSS
afu    ---MKSKGTRFERDLLVELWKAGFAAIRVAGSG-VSPFPCPDIVAGNGRTYLAIEVKMRK
mth    ---MVKNGTRGERDLVKLLWEKGFAAMRAPASGGATKKPLPDIIAGNGEIYLAIEVKTTA
              :*:  ***:*      *  ***.:*  ..  *        *  :.* pfu    KDHLYVGKRDMGRLIEFSRRFGGIPVLAVKFLNVGWRFIEVSPKI-----EKFVFTPSS--
pho    KGKLYIKGDDLKKLVEFANKFGGTPVLAVKFLGVGWRFFRPSGE------GNLVISPND--
mja    KTKFYINKEDIEKLISFSEIFGGKPYLAIKF-NGEMLFINPFLL-STNGKNYVIDERIKA
afu    ELPLYLSADEVEQLVTFARGFGAEAYVALKLPRKKWRFFPVQMLERTE-KNFKIDESVYP
mth    RERIYIDSEKIGALLRFSDIFGARPYIGIKFRYRDWIFLSPGDLELTPSSNYRLDLDIAL
          .  :  .   :   *: *    ** .  .   ::*:  .  *:        ..

pfu    --GVSL-EVLLGIQKTLE-GKS-
pho    --GETL-EVVVGLQRKLEVGEQK
mja    I-AIDFYEVI-GRGKQLKIDDLI
afu    L-GLEIAEVA-GKFFQERFGEKV
mth    ERGRDLDEVT-GNHRQTRLR---
            * **    .    .
```

SEQUENCE LISTING

```
<160> NUMBER OF SEQ ID NOS: 18

<210> SEQ ID NO 1
<211> LENGTH: 123
<212> TYPE: PRT
<213> ORGANISM: Pyrococcus furiosus

<400> SEQUENCE: 1

Met Tyr Arg Lys Gly Ala Gln Ala Glu Arg Glu Leu Ile Lys Leu
 1               5                  10                  15

Leu Glu Lys His Gly Phe Ala Val Val Arg Ser Ala Gly Ser Lys
                20                  25                  30

Lys Val Asp Leu Val Ala Gly Asn Gly Lys Lys Tyr Leu Cys Ile
                35                  40                  45

Glu Val Lys Val Thr Lys Lys Asp His Leu Tyr Val Gly Lys Arg
                50                  55                  60

Asp Met Gly Arg Leu Ile Glu Phe Ser Arg Arg Phe Gly Gly Ile
                65                  70                  75

Pro Val Leu Ala Val Lys Phe Leu Asn Val Gly Trp Arg Phe Ile
                80                  85                  90
```

```
                    Glu Val Ser Pro Lys Ile Glu Lys Phe Val Phe Thr Pro Ser Ser
                                    95                  100                 105

Gly Val Ser Leu Glu Val Leu Leu Gly Ile Gln Lys Thr Leu Glu
                                    110                 115                 120

Gly Lys Ser
                            123

<210> SEQ ID NO 2
<211> LENGTH: 369
<212> TYPE: DNA
<213> ORGANISM: Pyrococcus furiosus

<400> SEQUENCE: 2 atg tat aga aaa ggg gcc cag gca gag aga gaa ttg att aag ctc           45
Met Tyr Arg Lys Gly Ala Gln Ala Glu Arg Glu Leu Ile Lys Leu
 1               5                  10                  15 ttg gaa aag cat gga ttt gct gtg gtg agg tcg gca ggg agc aag           90
Leu Glu Lys His Gly Phe Ala Val Val Arg Ser Ala Gly Ser Lys
                20                  25                  30 aaa gtt gac tta gtt gca ggt aat gga aag aag tat ttg tgc ata           135
Lys Val Asp Leu Val Ala Gly Asn Gly Lys Lys Tyr Leu Cys Ile
                35                  40                  45 gaa gtt aag gtt aca aag aaa gat cat ttg tac gtg gga aag aga           180
Glu Val Lys Val Thr Lys Lys Asp His Leu Tyr Val Gly Lys Arg
                50                  55                  60 gac atg ggc aga tta ata gaa ttt tca aga agg ttt gga ggg atc           225
Asp Met Gly Arg Leu Ile Glu Phe Ser Arg Arg Phe Gly Gly Ile
                65                  70                  75 cca gtg ttg gct gtg aag ttc tta aat gtt ggg tgg agg ttt att           270
Pro Val Leu Ala Val Lys Phe Leu Asn Val Gly Trp Arg Phe Ile
                80                  85                  90 gag gta agc cca aaa att gag aag ttt gtc ttc acg cct tct agc           315
Glu Val Ser Pro Lys Ile Glu Lys Phe Val Phe Thr Pro Ser Ser
                95                  100                 105 gga gta tct ctt gag gta ttg ttg gga ata caa aaa acg ttg gag           360
Gly Val Ser Leu Glu Val Leu Leu Gly Ile Gln Lys Thr Leu Glu
                110                 115                 120 ggg aaa tca                                                           369
Gly Lys Ser
        123

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
cctgcaggat ggtaggacgg cctcgcaatc ccgattgacc gagcacgcga gatgtcaacg     60
atcgaattgc                                                            70

<210> SEQ ID NO 4
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
```

```
gcaattcgat cgttgacatc tcgcgtgctc ggtcaatcgg cagatgcgga gtgaagttcc      60
aacgttcggc                                                              70

<210> SEQ ID NO 5
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
gccgaacgtt ggaacttcac tccgcatctg ccgattgacc gagtggcgtg tttctggtgg      60
ttcctaggtc                                                              70

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
gacctaggaa ccaccagaaa cacgccactc ggtcaatcgg gattgcgagg ccgtcctacc      60
atcctgcagg                                                              70

<210> SEQ ID NO 7
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
gccgaacgtt ggaacttcac tccgcatctg ccgattgacc gagcacgcga gatgtcaacg      60
atcgaattgc                                                              70

<210> SEQ ID NO 8
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
cctgcaggat ggtaggacgg cctcgcaatc ggcttcgacc gagcacgcga gatgtcaacg      60
atcgaattgc                                                              70

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
gccgaacgtt ggaacttcac tccgcatctg ccgattctgg ctgtggcgtg tttctggtgg      60
ttcctaggtc                                                              70
```

<210> SEQ ID NO 10
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
gacctaggaa ccaccagaaa cacgccacag ccaggaagcc gattgcgagg ccgtcctacc    60
atcctgcagg                                                          70

<210> SEQ ID NO 11
<211> LENGTH: 68
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
gacctaggaa ccaccagaaa cacgccactc ggtcgaccga gcacgcgaga tgtcaacgat    60
cgaattgc                                                            68

<210> SEQ ID NO 12
<211> LENGTH: 68
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
gacctaggaa ccaccagaaa cacgccacag ccaggaccga gcacgcgaga tgtcaacgat    60
cgaattgc                                                            68

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
gccgaacgtt ggaacttcac tccgcatctg gagcacgcga gatgtcaacg atcgaattgc    60

<210> SEQ ID NO 14
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
gccgaacgtt ggaacttcac tccgcatctg ccgatggacc gagcacgcga gatgtcaacg    60
atcgaattgc                                                          70

<210> SEQ ID NO 15
<211> LENGTH: 59
<212> TYPE: DNA
<213> ORGANISM: Artificial Sequence

```
<220> FEATURE:
<223> OTHER INFORMATION: Description of Artificial Sequence:
      Oligonucleotide

<400> SEQUENCE: 15
gcaattcgat cgttgacatc tcgcgtgctc ggtcaatcgg cagatgcgga gtgaagttc         59

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
gaacttcact ccgcatctgc cgattgaccg agtggcgtgt ttctggtggt tcctaggtc         59

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
cgtcgcacga gcatatgtat agaaaagggg ccc                                     33

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
cgcacgagga tatcttatca tgatttcccc tccaac                                  36
```

US 6,277,614 B1

DEOXYRIBONUCLEASE

BACKGROUND OF THE INVENTION

1. Field of the Invention

The present invention relates to a useful deoxyribonuclease as a reagent for gene manipulation and to a process for producing said enzyme using genetic engineering techniques.

2. Description of the Related Art

The enzymes most frequently used as deoxyribonucleases that recognize specific sequences and cleave double-stranded DNAs (that is, genes), base sequence-specifically, are those called restriction enzymes, and they typically recognize the sequences of 4 to 8 bases. Restriction enzymes have played essential roles in genetic engineering experiments: they have been used in daily gene manipulation experiments, and thereby greatly contributed to advances in molecular medicine, molecular biology, and biochemistry.

In addition to restriction enzymes, as enzymes that recognize nucleotide sequence and cleave double-stranded DNAs, there is a group of enzymes called homing endonucleases, which are involved in the DNA recombination process. Although these enzymes generally require sequences as long as 20 or more bases for recognition, recognized sequences are specific for respective enzymes, and therefore, these enzymes can be used for the purpose of site-specific DNA cleavage.

Thus, there have been many practical applications of enzymes that recognize and cleave DNA sequences. As to enzymes that recognize and cleave specific steric structures of DNA, however, only few studies are known with particular emphasis on *Escherichia coli* RuvC protein, and there are no enzymes that have already come into practical use, although biochemical properties such as substrate specificity have been elucidated to some extent.

Although several enzymes that recognize and cleave a specific steric structure such as the Holliday structured are presently known, they are all derived from mesophilic organisms, and their thermostability or cleavage efficiency in vitro is low. An object of the present invention is to develop a practical enzyme that specifically recognize and cleave a Holliday structured DNA, which is a DNA recombination intermediate, to resolve it into two sets of double-stranded DNAs, and to provide such enzyme as a reagent for gene manipulation.

SUMMARY OF THE INVENTION

The present inventors have discovered, as a result of their extensive study, a novel protein having deoxyribonuclease activity from a hyperthermophilic archaebacterium, *Pyrococcus furiosus*, and succeeded in cloning the gene encoding said protein. Furthermore, the present inventors have succeeded in preparing a transformant into which the gene has been introduced, and in producing said protein on a large scale.

Thus, the present invention relates to a protein which is thermostable and which has deoxyribonuclease activity that specifically acts on and cleaves a Holliday structured DNA, which is an intermediate structure in the DNA recombination process, to resolve it into two sets of double-stranded DNAs.

The present invention also relates to a gene encoding said protein.

The present invention further relates to a process for producing said protein, comprising:

1) preparing said gene,
2) constructing an expression vector by inserting said gene into a vector,
3) transforming host cells with said vector,
4) culturing said transformants, and
5) isolating said protein from said culture.

The present inventors have screened archaebacteria for a protein having activity that specifically cleaves an artificially synthesized Holliday structured DNA to resolve it into two sets of double-stranded DNAs, with the aim of isolating a resolvase that specifically recognize and cleave a Holliday structured (cruciform structure) DNA, which is an intermediate in the DNA recombination process. As a result, the present inventors have discovered a protein having desired properties from *Pyrococcus furiosus*, a species of hyperthermophilic archaebacteria.

The gene region encoding the protein was cloned, and determination of the base sequence of the gene obtained revealed a small open reading frame (ORF) consisting of 123 amino acids. Only the ORF was then subcloned, and the protein was produced in *E. coli*. The protein obtained was purified until an electrophoretically single band was obtained, and its substrate specificity was studied in detail. In result, it was found that the enzyme has the desired activity that specifically recognizes and cleaves only four-way junction Holliday structured as shown in FIG. 1 or 2. The other structures such as single-stranded, double-stranded, loop-out structures, a single base mismatch, and the like were not cleaved, although, in some cases, a quite small amount of cleavage products was observed with three-way junction structures. When a large excess (10-fold equivalents) of the enzyme was added to the reaction, the cleavage efficiency for the three-way junction structures was enhanced, and also the loop-out structure was slightly cleaved.

Regarding the cleavage pattern of the Holliday structured, it was confirmed, based on the re-ligation of cleaved DNA strands by DNA ligase reaction, that a phosphodiester bond is cleaved into 5'-phosphate and 3'-OH forms.

Based on the above results, it was concluded that the protein is a novel, DNA steric structure-specific deoxyribonuclease, and the protein was named "Pfu-HJC endonuclease". Database search regarding amino acid sequence revealed that no proteins having known functions that exhibit a significant homology (or genes encoding the same) have been registered. However, an ORF having a highly homologous sequence was found in all the four archaebacteria of which entire genomic sequences have been decoded to date (*Methanococcus jannaschii*, *Archaeoglobus fulgidus*, *Methanobacterium thermoautotrophicum*, and *Pyrococcus horikoshii*), strongly suggesting that the enzyme may be an important enzyme that is conserved at least among archaebacteria.

BRIEF DESCRIPTION OF THE DRAWINGS

FIG. 5 shows DNA having a loop-out structure, prepared in order to study the substrate specificity of Pfu-HJC endonuclease. The positions marked by arrowheads indicate the cleavage points demonstrated in (2) of Example 4, and the size of arrowhead represents the degree of cleavage.

Pfu: *Pyrococcus furiosus* cell extract, RuvC: *E. coli* RuvC protein (known to have enzymatic activity cleaving Holliday structured). As a control, reactions in which a conventional double-stranded DNA (70-mer) was used as a substrate were analyzed.

FIG. 7 shows an exemplary experiment in which the substrate specificity of Pfu-HJC endonuclease was studied. Using DNAs exhibiting various structures schematically represented in the figure, cleavage reactions were performed with Pfu-HJC endonuclease. The reactants were then separated by electrophoresis on a denaturing polyacrylamide gel containing 8 M urea, and detected by autoradiography. The sites of cleavage were also determined by the mobilities of the bands in comparison with size markers.

FIG. 8 shows the results of analysis on the cleavage pattern by Pfu-HJC endonuclease. As shown on the left panel, Pfu-HJC endonuclease reaction was performed using, as a substrate, a Holliday structure prepared by combining DNAs having different chain lengths, and DNA ligase was then added to the products to confirm that ligation at the cleavage points was observed. The reactants were separated by electrophoresis on a denaturing polyacrylamide gel containing 8 M urea, and detected by autoradiography. Such a re-ligation as shown on the left panel should generate a 70-mer DNA, and indeed, a 70-mer band was confirmed by the DNA ligase reaction.

FIG. 9 shows archaebacterium-derived gene products having homologies to the amino acid sequence of Pfu-HJC endonuclease.

Besides *Pyrococcus furiosus*, homologous open reading frames were found in the four other archaebacteria. Pfu: *Pyrococcus furiosus*, Pho: *Pyrococcus horikoshii*, Mja: *Methanococcus jannaschii*, Afu: *Archaeoglobus fulgidus*, and Mth: *Methanobacterium thermoautotrophicum*. Among the positions conserved in all the five species, those positions containing an identical amino acid residues are indicated by asterisks, those positions containing similar amino acid residues are indicated by double-dots, and those positions conserved among three or more species are indicated by single-dots.

Figure 10:
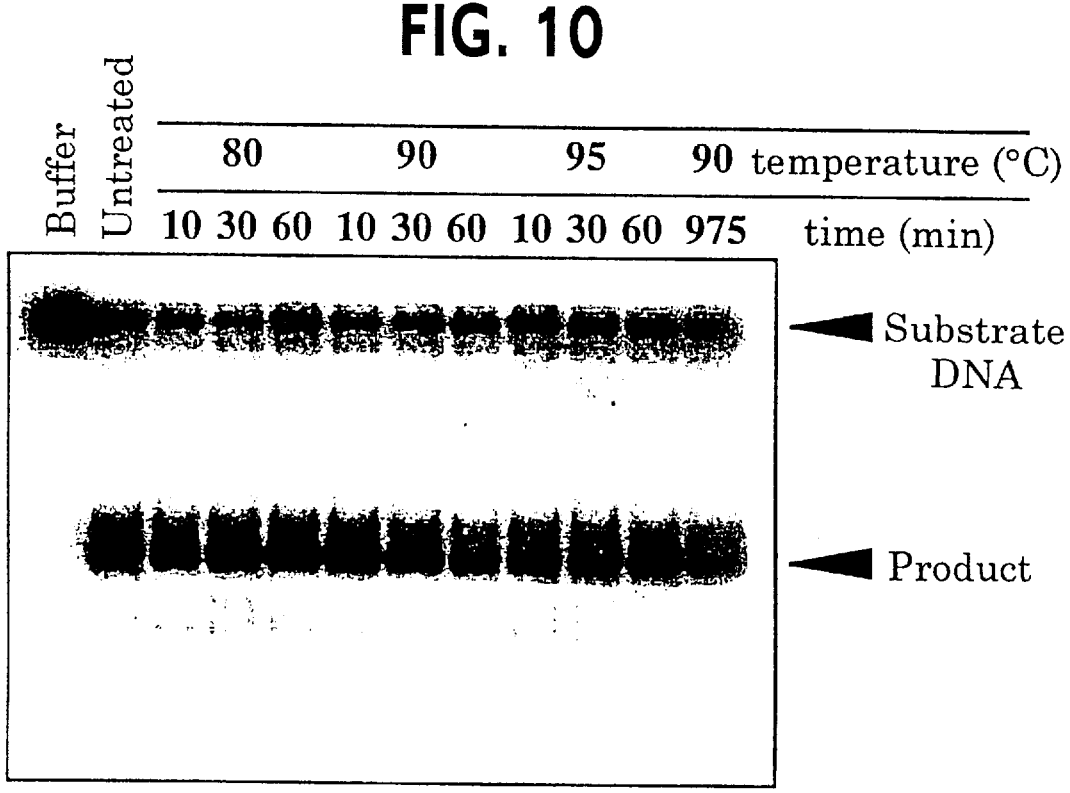

FIG. 10 shows the results of analysis on thermostability of Pfu-HJC endonuclease. Pfu-HJC endonuclease heat-treated at the temperature and for the period indicated in the figure was used to perform a cleavage reaction with the artificial Holliday structured DNA (radiolabeled) shown in FIG. 1. The reactants were then separated by 12% polyacrylamide gel electrophoresis, and detected by autoradiography. (Buffer: Buffer A, Untreated: reaction by Pfu-HJC endonuclease with no heat-treatments.)

DESCRIPTION OF THE PREFERRED EMBODIMENTS

The protein of the present invention is thermostable, and has deoxyribonuclease activity that specifically acts on and cleaves a Holliday structured DNA, which is an intermediate structure in the DNA recombination process, to resolve it into two sets of double-stranded DNA.

Figure 1:
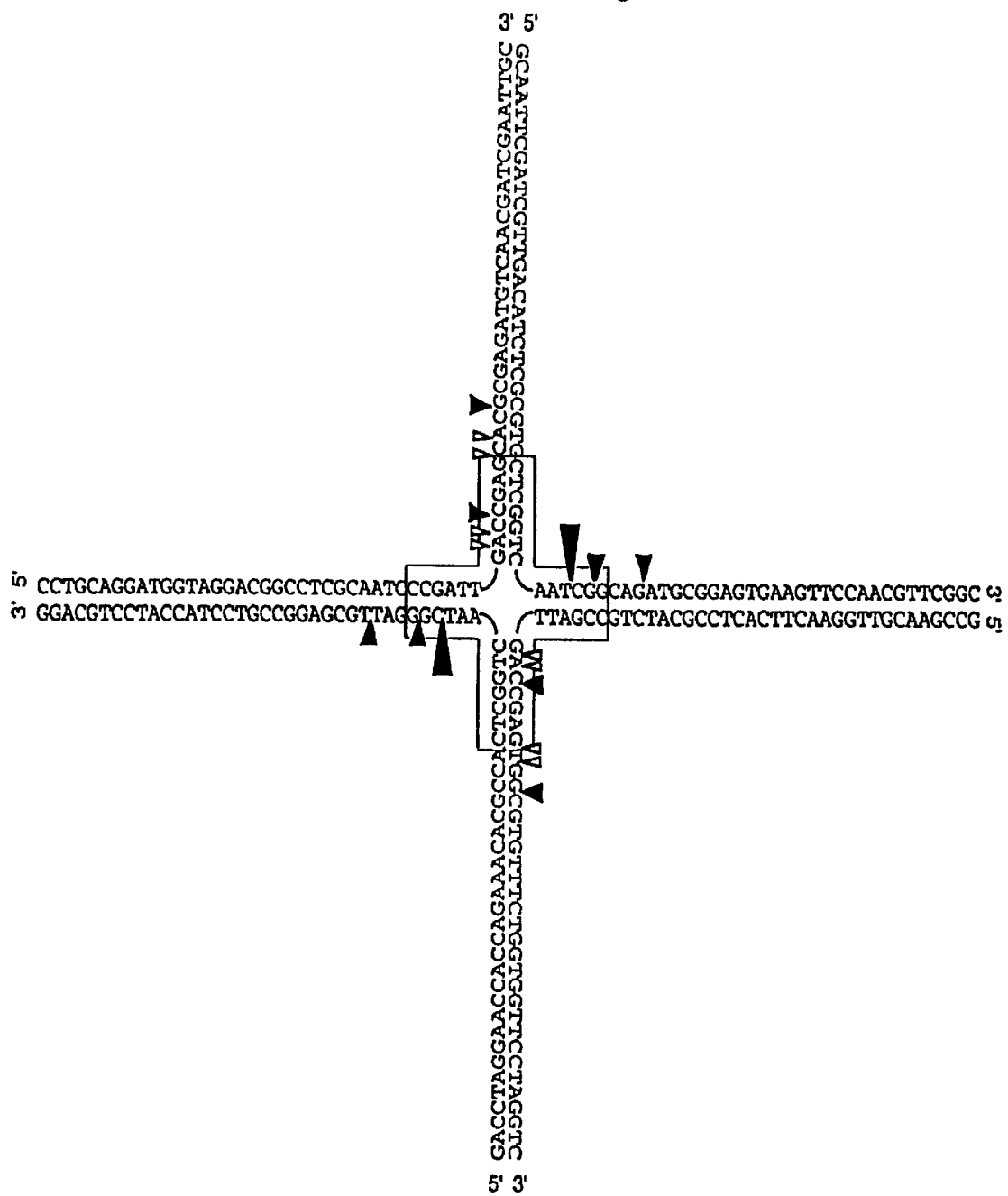
FIG. 1 shows an artificial Holliday structured DNA of which center migrates, used in the screening for Pfu-HJC endonuclease. The box in the figure indicates the sequence in which the branch point can migrate. The positions marked by arrowheads indicate the cleavage points demonstrated in (2) of Example 4, and the size of arrowhead represents the degree of cleavage.
Figure 2:
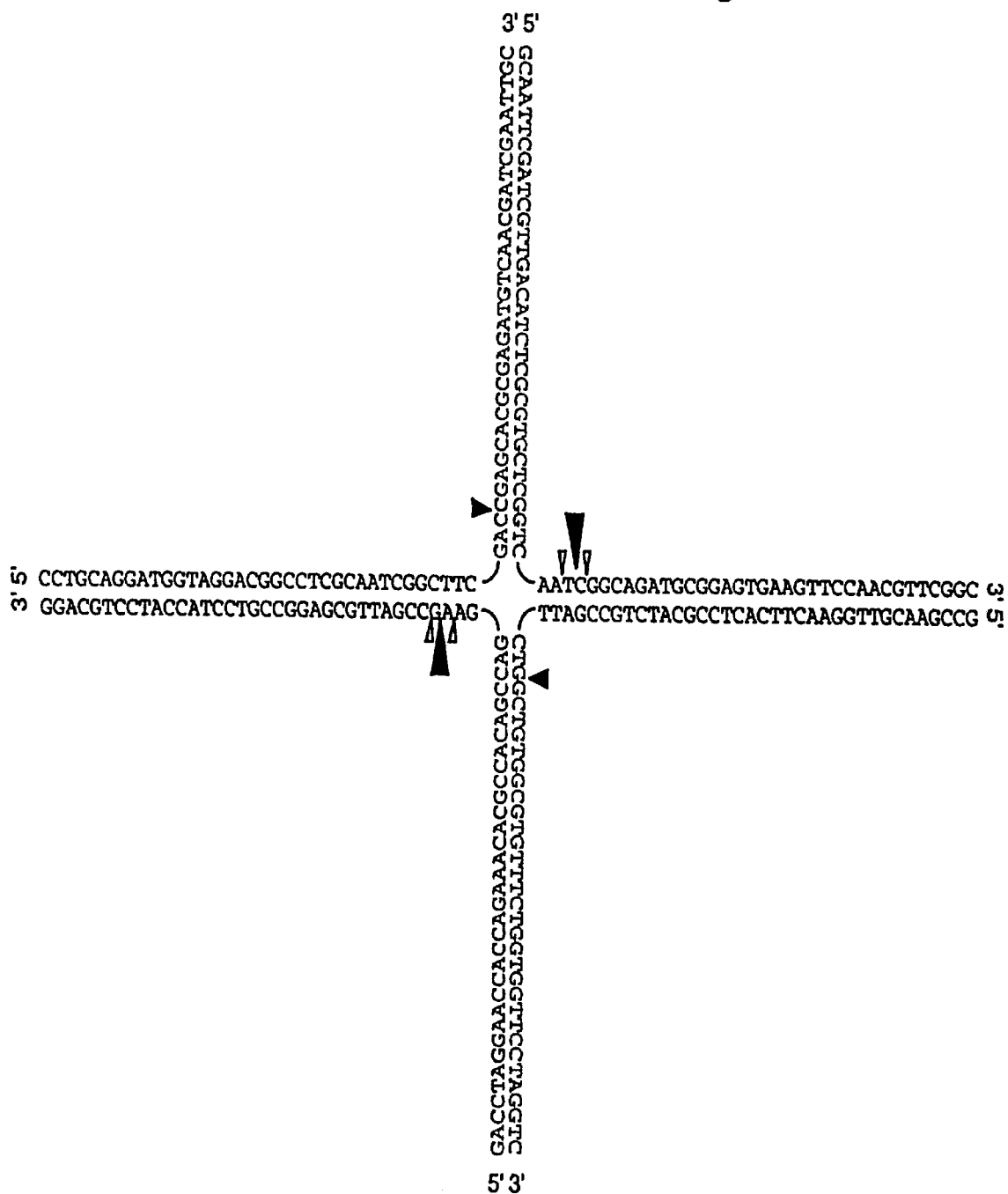
FIG. 2 shows an artificial Holliday structured DNA of which center does not migrate, used in the screening for Pfu-HJC endonuclease. The positions marked by arrowheads indicate the cleavage points demonstrated in (2) of Example 4, and the size of arrowhead represents the degree of cleavage.

For example, the protein has enzymatic activity that recognizes DNA having a four-way junction Holliday structure as shown in FIG. 1 or 2, and cleaves it so as to generate two separate sets of double-stranded DNAs (see FIG. 8). The protein is thermostable; that is, the above activity is retained at least even after incubation at 95° C. for one hour or at 90° C. for 16 hours.

In one embodiment, the protein of the present invention is 1) a protein having the amino acid sequence of SEQ ID NO: 1 or 2) a protein having an amino acid sequence wherein one to several amino acids are deleted, substituted, or added in the amino acid sequence of SEQ ID NO: 1.

The present invention also relates to a gene that encodes 1) a protein having the amino acid sequence of SEQ ID NO: 1 or 2) a protein having an amino acid sequence wherein one to several amino acids are deleted, substituted, or added in the amino acid sequence of SEQ ID NO: 1, wherein the protein has deoxyribonuclease activity that specifically acts on and cleaves a Holliday structured DNA, which is an intermediate structure in the DNA recombination process, to resolve it into two sets of double-stranded DNAs.

The gene is preferably derived from thermostable bacteria, and preferably has the base sequence of SEQ ID NO: 2.

The present invention further relates to a gene which is capable of hybridizing to the gene shown in SEQ ID NO: 2 under stringent conditions and which encodes a protein having deoxyribonuclease activity that specifically acts on and cleaves a Holliday structured DNA, an intermediate structure in the DNA recombination process, to resolve it into two sets of double-stranded DNAs.

One can determine whether a gene is capable of hybridizing under stringent conditions or not, as follows. Firstly, DNAs subjected to hybridization are immobilized onto a nylon membrane. Next, the membrane is immersed in a pre-hybridization solution containing 6×SSC, 0.01 M EDTA, 5×Denhardt's solution, 0.5% SDS, and 100 μg/ml denatured salmon DNA at 68° C. for 2 hours. A solution (hybridization solution) is prepared by adding the labeled gene shown in SEQ ID NO: 2 or the corresponding RNA, which is a transcription product of said gene, to the pre-hybridization solution having the above composition. In this solution, the nylon membrane obtained above is immersed, and hybridization is conducted at 68° C. for 3 to 16 hours. The membrane is then washed by soaking it in a solution containing 2×SSC, 0.5% SDS, and further washed in a 2×SSC, 0.1% SDS solution at room temperature for about 15 minutes. Furthermore, the membrane is washed in a 0.5% or 0.1% SDS solution at 68° C. for 2 hours. Then, a detecting step is conducted using an appropriate mean depending on the label.

Examples of such genes may include DNAs encoding the amino acid sequences shown in FIG. 9.

The protein of the present invention may be prepared according to the following procedures using well-known DNA recombinant techniques (see, for example, Maniatis et al., Molecular Cloning A Laboratory Manual, 2nd Ed., Chapter 15, Cold Spring Harbor Laboratory Press, 1989):

1) preparing a gene that encodes a protein having the amino acid sequence of SEQ ID NO: 1 or an amino acid sequence wherein one to several amino acids are deleted, substituted, and/or added in the amino acid sequence of SEQ ID NO: 1 (techniques for deleting, substituting, or adding amino acids are well known to those skilled in the art. Details for such methods are described in the above reference),
2) constructing an expression vector by inserting the above gene into an appropriate vector,
3) transforming host cells with the above expression vector,
4) culturing the transformed host cells, and
5) isolating the protein of the present invention from the above culture.

A transformant obtained by introducing a plasmid pPFHJC1, which incorporated a gene encoding the protein of the present invention into an expression vector for *E. coli*, pET21a (Novagene, Inc.), into *E. coli* BL21 (DE3) was designated and labeled as Escherichia coli BL21 (DE3)/pPFHJC1, and has been deposited at National Institute of Bioscience and Human-Technology, Agency of Industrial Science and Technology under Deposit No. FERM BP-6915.

Pfu-HJC endonuclease is the first Holliday junction DNA resolvase isolated from a hyperthermophilic organism, and the isolated and purified enzyme exhibits thermostability. As advantages of the ability to carry out reactions at elevated temperatures, it is expected that the cleavage efficiency may be better than that of conventional mesophilic enzymes, and further, that the secondary structure of a substrate DNA based on its base sequence may have smaller influence on the cleavage efficiency.

EXAMPLES

The present invention is described in more detail by the following examples, but not limited to such examples.

Example 1

(1) Preparation of *Pyrococcus furiosus* Genomic DNA

*P. furiosus* DSM 3638 was obtained from Deutsche Sammlung von Mikroorganismen und Zelkulturen GmbH, and cultured according to the method described in the literature (Nucleic Acids Research, vol. 21, pp. 259–265). About 1.2 g of cells was obtained from 500 ml of culture liquid.

The cells were suspended in 10 ml of Buffer L (10 mM Tris-HCl (pH 8.0), 1 mM EDTA, 100 mM NaCl), and 1 ml of 10% SDS was added thereto. After stirring, 50 μl of proteinase K (20 mg/ml) was added, and allowed to stand at 55° C. for 60 minutes. Subsequently, the reaction liquid was successively subjected to phenol extraction, phenol/chloroform extraction, and chloroform extraction. Ethanol was then added to insolubilize DNA. The DNA recovered was dissolved in 1 ml of TE solution (10 mM Tris-HCl (pH 8.0), 1 mM EDTA), 0.75 mg of RNase A was added thereto, and allowed to react at 37° C. for 60 minutes. Then, the reaction liquid was again subjected to phenol extraction, phenol/chloroform extraction, and chloroform extraction, followed by ethanol precipitation to recover DNA. 0.75 mg of DNA was obtained.

(2) Preparation of a Cosmid Library

Using SuperCos 1 Cosmid Vector kit manufactured by Stratagene, a gene library was prepared according to the instruction for use. The reaction conditions were determined so as to generate fragments of 30–42 kilobase-pairs when DNA obtained in (1) was partially digested with a restriction enzyme, Sau3AI. The DNA fragments obtained after digestion were inserted into the BamHI site of the cosmid vector to construct a library of recombinant cosmids. A dozen colonies were randomly selected from the colonies obtained by transformation of *E. coli*, and cosmids were recovered to confirm that DNA fragments having expected sizes have been inserted.

(3) Preparation of Crude Extracts From the Library

From the transformants prepared in (2) using recombinant cosmids, about 500 colonies were selected and each cultured in 2 ml of LB medium. After harvesting, the cells were suspended in 500 ml of Buffer A (10 mM Tris-HCl (pH 8.0), 2 mM 2-mercaptoethanol, 10% glycerol), and then disrupted by sonication. The crude extracts obtained were heat-treated at 85° C. for 10 minutes to denature most of proteins derived from *E. coli*, and the supernatants were collected by centrifugation as a thermostable protein library.

Example 2

(1) Reaction Forming Holliday Structured DNAs

A hundred pmol of the DNA shown in SEQ ID NO: 4 of Sequence Listing was 5'-end phosphorylated using polynucleotide kinase and [$\gamma$-$^{32}$P]-ATP. A 30 pmol aliquot thereof was then mixed with equal amounts of DNAs shown in SEQ ID NOs: 3, 5, and 6, heat-treated at 65° C. for 30 minutes, and allowed to gradually cool by itself over 15 hours to room temperature to form the four-way junction structure, of which center migrates, shown in FIG. 1. For the purpose of a control experiment, the end-labeled DNA shown in SEQ ID NO: 4 was similarly mixed with an equal amount of the DNA shown in SEQ ID NO: 7 to form a double-stranded DNA.

In order to examine the substrate specificity, end-labeled DNA shown in SEQ ID NO: 4 was mixed with equal amounts of DNAs shown in SEQ ID NOs: 8, 9, and 10 to form a four-way junction structure of which center does not migrate; with DNAs shown in SEQ ID NOs: 5 and 11 to form a three-way junction structure of which center migrates; with DNAs shown in SEQ ID NOs: 9 and 12 to form a three-way junction structure of which center does not migrate; with the DNA shown in SEQ ID NO: 13 to form a loop-out structure; with the DNA shown in SEQ ID NO: 14 to form a single base mismatch; and with SEQ ID NO: 3 or 5 to form a half-double/half-single stranded DNA.

Figure 3:
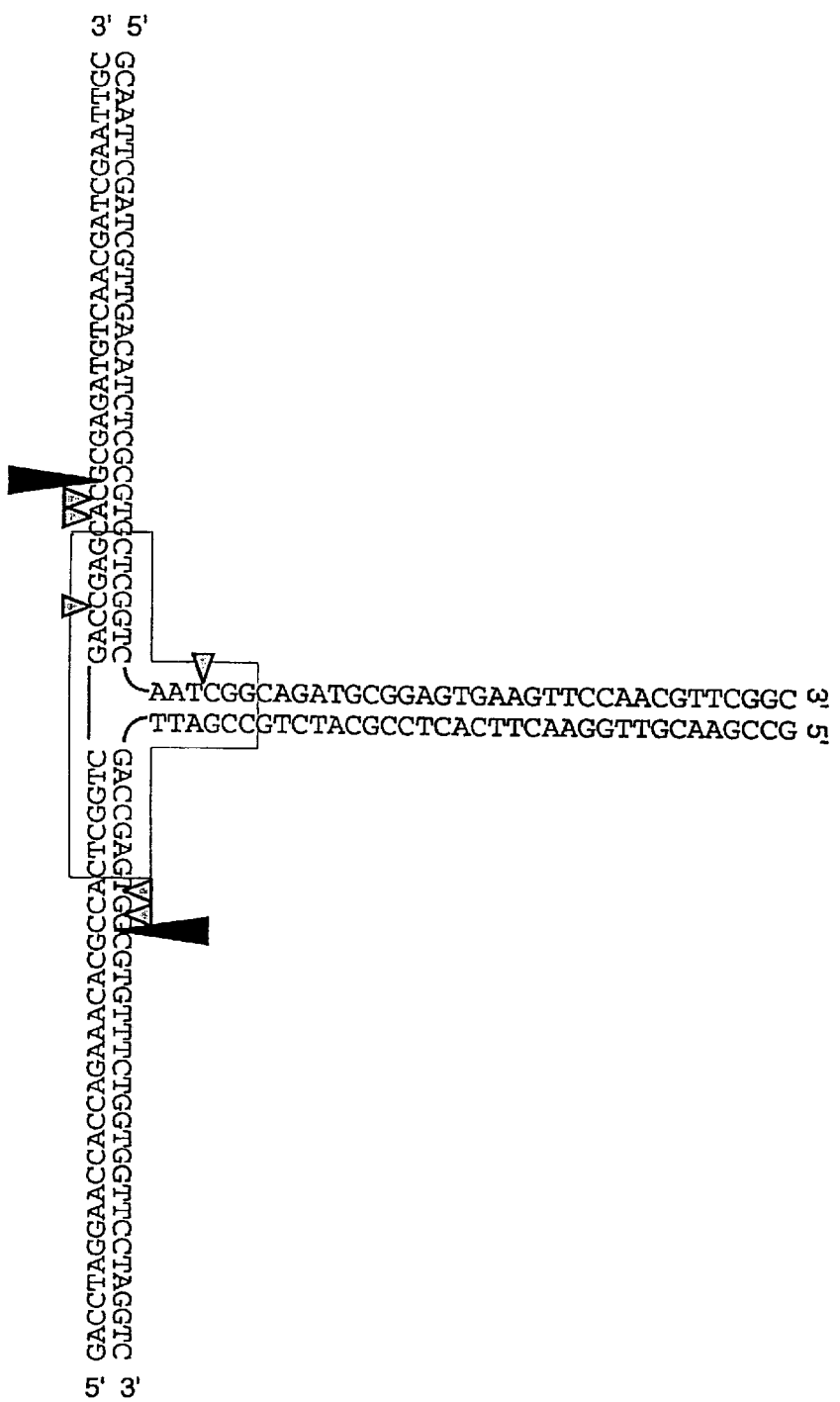
FIG. 3 shows a three-way junction DNA of which center migrates, prepared in order to study the substrate specificity of Pfu-HJC endonuclease. The box in the figure indicates the sequence in which the branch point can migrate. The positions marked by arrowheads indicate the cleavage points demonstrated in (2) of Example 4, and the size of arrowhead represents the degree of cleavage.
Figure 4:
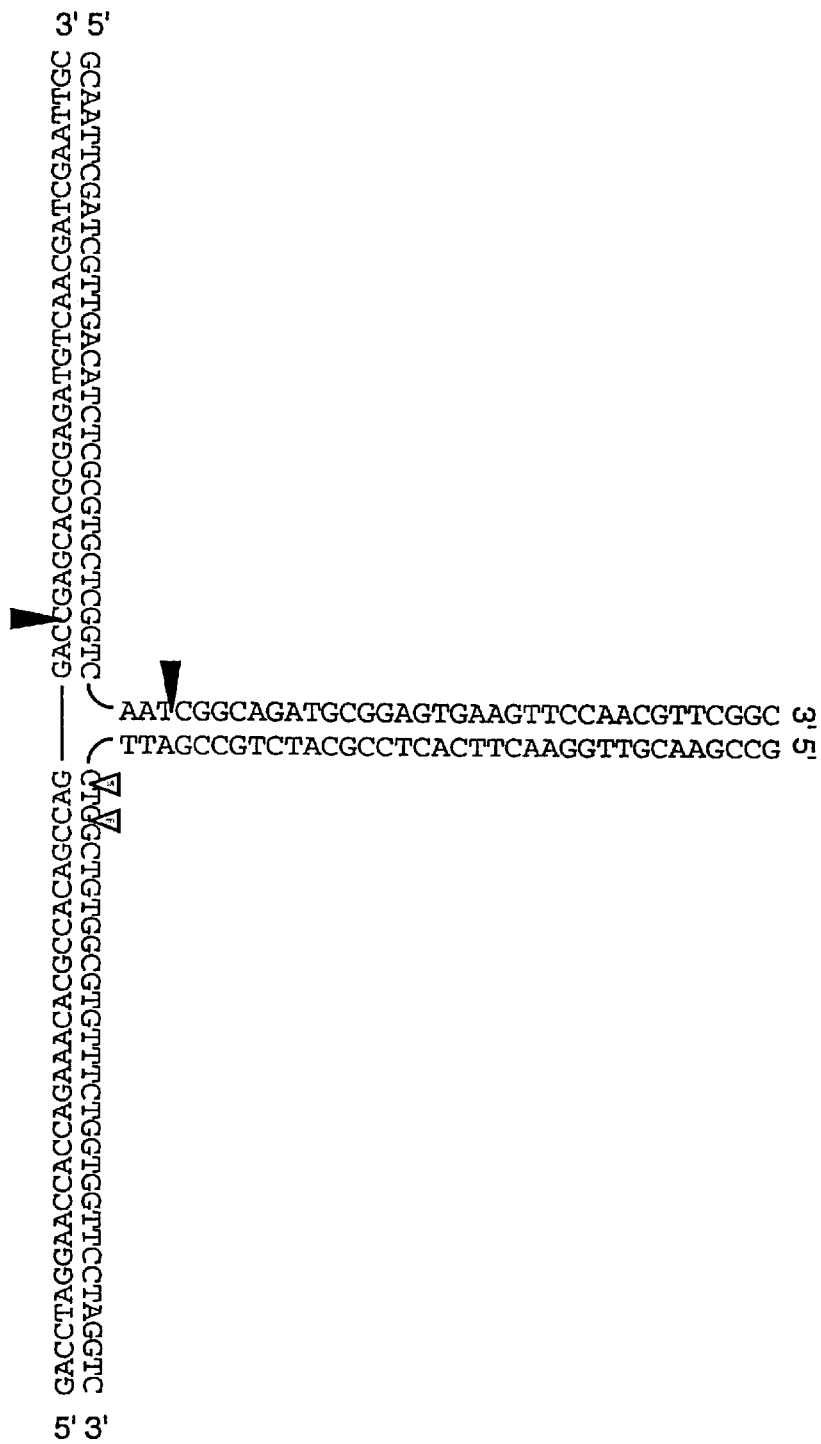
FIG. 4 shows a three-way junction DNA of which center does not migrate, prepared in order to study the substrate specificity of Pfu-HJC endonuclease. The positions marked by arrowheads indicate the cleavage points demonstrated in (2) of Example 4, and the size of arrowhead represents the degree of cleavage.

In order to determine the sites of cleavage in those structures, among these substrates, that have been demonstrated to be cleaved, the four-way junction structure of which center migrates (FIG. 1), the four-way junction structure of which center does not migrate (FIG. 2), the three-way junction structure of which center migrates (FIG. 3), the three-way junction structure of which center does not migrate (FIG. 4), and the loop-out structure (FIG. 5), wherein respective arms to be analyzed have been labeled at their ends, were each formed as described above. In addition, to determine the cleavage pattern, the DNA shown in SEQ ID NO: 15 was mixed with DNAs shown in SEQ ID NOs: 3, 6, and 16, after end-labeled as described above, to form the four-way junction structure in which the labeled arm was short.

(3) Holliday Structured DNA Cleavage Reaction

A solution consisting of 10 mM Tris-HCl (pH 8.8), 10 mM MgCl$_2$, 1 mM dithiothreitol, 200 mM KCl, and 10 nM $^{32}$P-labeled four-way junction DNA of which center migrates was prepared as a reaction solution, and to 36 μl of this solution, 4 μl of *Pyrococcus furiosus* cell crude extract was added. After reacting at 56° C. for 30 minutes, the reaction was stopped by phenol/chloroform.

Figure 6:
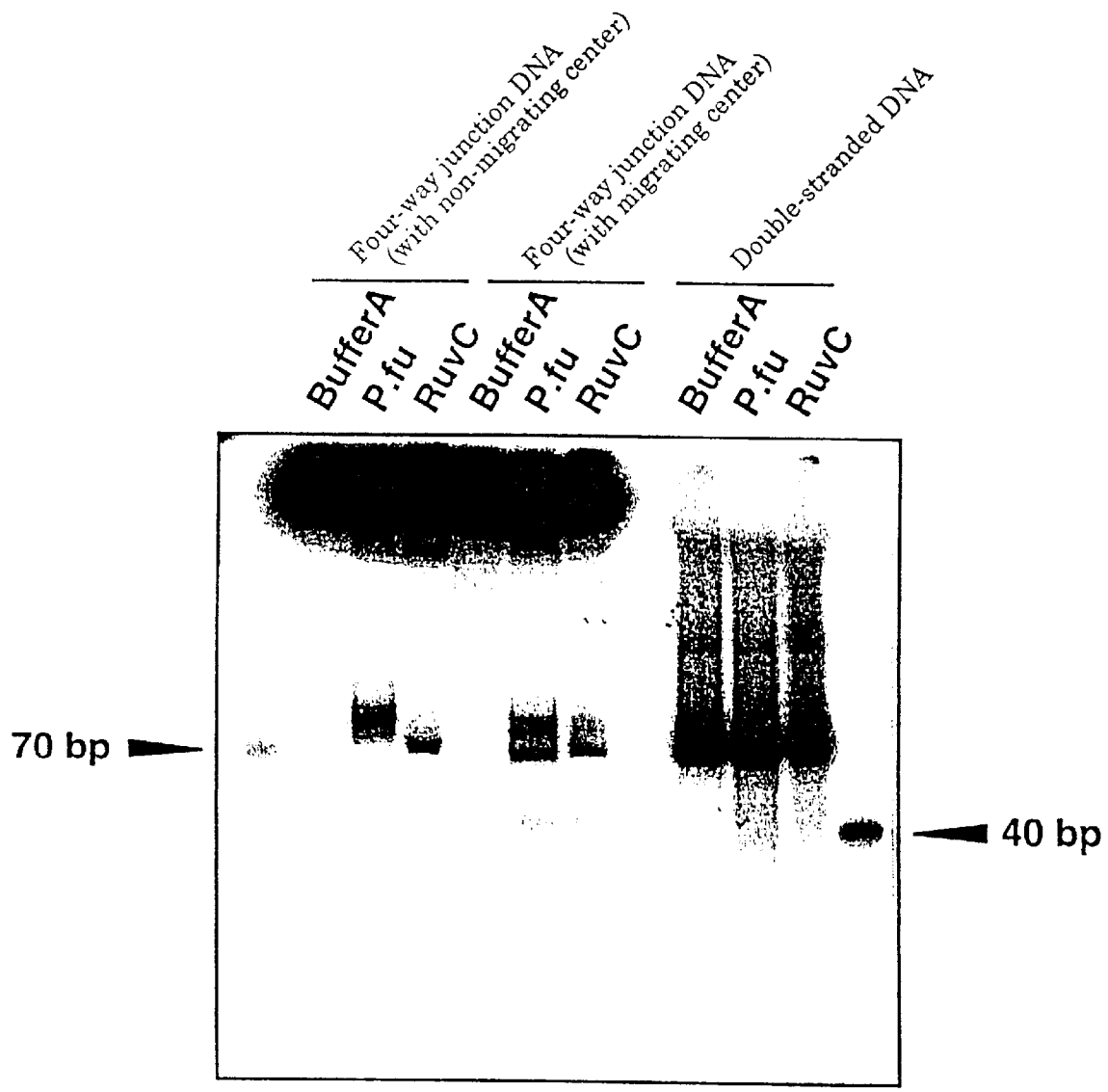
FIG. 6 shows detection of the Pfu-HJC endonuclease activity. After conducting cleavage reactions using two types of artificial Holliday structured DNAs shown in FIGS. 1 and 2 (radiolabeled), the reactants were separated by 12% polyacrylamide gel electrophoresis, and detected by autoradiography.

To 20 μl of the supernatant, 5 μl of loading buffer [0.025% xylene cyanol, 0.025% bromophenol blue, 40% (w/v) sucrose] was added, and a 5 μl aliquot of the mixture was electrophoresed on 12% acrylamide gel in TAE buffer [40 mM Tris-acetate (pH 8.0), 1 mM trisodium ethylenediaminetetraacetate]. After drying, the acrylamide gel was subjected to autoradiography to determine the presence or absence of cleavage bands. In result, activity that cleaves the four-way junction structure DNA was found in *Pyrococcus furiosus* cell crude extract (FIG. 6).

(4) Screening of the Thermostable Protein Library for Desired Cleavage Activity

To 36 μl of the above-described reaction solution, each 0.8 μl of extracts for 5 clones from the thermostable protein library (i.e., a total of 4 μl per reaction) was added, reacted at 56° C. for 30 minutes, and the reaction was then stopped by phenol/chloroform. The supernatant was electrophoresed as described above, and autoradiography was performed to determine the presence or absence of cleavage bands. In result, activity that cleaves the four-way junction structure DNA was found in 5 clones: clone Nos. 25, 463, 465, 469, and 473.

Example 3

(1) Identification and Nucleotide Sequencing of the Objective Gene

Of the clones obtained in (4) of Example 2, No. 463 was used to isolate the cosmid. The cosmid isolated was digested with BssHII existing in the cosmid, then partially digested with EcoRI, and subcloned into pUC118 vector. For each clone obtained, its Holliday structured DNA cleaving activity was examined as in (3) of Example 2, and it was found that a clone into which an about 6 kb EcoRI-EcoRI fragment has been incorporated exhibited the cleaving activity. The pUC118 vector incorporating said EcoRI-EcoRI fragment was named plasmid pFU100.

Using plasmid pFU100, deletion mutants were successively prepared from the both ends of the inserted DNA. For the preparation, Deletion Kit for Kilo-Sequencing (Takara Shuzo Co., Ltd.) was used. The nucleotide sequence of the inserted fragment was determined using DNA Sequencing Kit (Perkin Elmer) with various deletion mutants obtained, as templates.

Using plasmid pFU100, deletion mutants were prepared taking advantage of restriction enzyme sites. Various deletion mutants obtained were examined as described above for their Holliday structured DNA cleaving activities, and a single ORF corresponding to the cleaving activity was defined.

(2) Construction of a Over Expression System for the Objective Gene

On the basis of the nucleotide sequences at the both ends of the ORF, in the base sequence obtained in (1) of Example 3, that appeared to be derived from Holliday structured DNA cleaving activity, PCR primers shown in SEQ ID NOs: 17 and 18 of Sequence Listing were prepared so that NdeI (CATATG) and EcoRV (GATATC) sequences were incorporated into the forward and reverse primers, respectively, and that ATG in the NdeI sequence can be used as a translational initiation codon. The gene amplified by PCR method was incorporated into pET21a vector to obtain a plasmid producing an enzyme that specifically cleaves four-way junction DNAs, and the plasmid was named pPFHJC1 after confirming the nucleotide sequence of the region in the plasmid that has been amplified by PCR contained no changes. In addition, *E. coli* BL21(DE3) transformed with said plasmid was named *Escherichia coli* BL21(DE3)/pPFHJC1.

(3) Preparation and Purification of the Objective Enzyme Protein

*Escherichia coli* BL21(DE3)/pPFHJC1 obtained in (2) of Example 3 was cultured in 500 ml of LB medium [tryptone 10 g/liter, yeast extract 5 g/liter, NaCl 5 g/liter, pH 7.2] containing ampicillin at a concentration of 100 μg/ml. When the absorbance of the culture liquid reached 0.7 $A_{600}$, an inducer, isopropyl-β-D-thiogalactoside (IPTG), was added, and further cultured for three hours.

After harvesting, the cells were suspended in 30 ml of Buffer A supplemented with 1 mM phenylmethylsulfonyl fluoride (PMSF), and subjected to a sonicator. The crude exact was recovered as a supernatant by centrifugation at 16,000 rpm for 20 minutes, and ammonium sulfate was added thereto so as to attain 80% saturation. The precipitate obtained by centrifugation at 16,000 rpm for 20 minutes was dissolved in 30 ml of Buffer A, and ammonium sulfate was again added thereto so as to attain 80% saturation. The precipitate obtained by centrifugation at 16,000 rpm for 20 minutes was dissolved in 10 ml of Buffer A, and dialyzed with 2 liters of Buffer A. The dialyzed solution was heat-treated at 80° C. for 15 minutes, and the supernatant was recovered by centrifugation at 16,000 rpm for 20 minutes. Ten ml of this solution was applied to a HiTrap Q column (Pharmacia) equilibrated with Buffer A, and chromatographed using the FPLC system (Pharmacia). Development was performed with a linear gradient of NaCl concentration from 0 M to 1 M. The desired activity was eluted at 0.5–0.8 M NaCl. A 10 ml fraction containing the activity was collected, dialyzed with 2 liters of Buffer B [10 mM potassium phosphate (pH 6.8), 7 mM 2-mercaptoethanol, 0.05 mM KCl, 10% glycerol], and applied to a CHT-II column (Bio-Rad) equilibrated with Buffer B. When developed with a linear gradient of phosphate concentration from 0.01 M to 1 M using the FPLC system, the desired activity was eluted at 0.6–0.8 M phosphate. This fraction was dialyzed with 2 liter of Buffer A to obtain a purified preparation, which was designated Pfu-HJC endonuclease. From 500 ml of the culture liquid, about 1 mg of the enzyme was obtained.

Example 4

(1) Substrate Specificity

In order to study the substrate specificity in DNA cleavage by Pfu-HJC endonuclease of the present invention, the four-way junction structure of which center migrates, the four-way junction structure of which center does not migrate, the three-way junction structure of which center migrates, the three-way junction structure of which center does not migrate, the loop-out structure, a single base mismatch, and half-double/half-single stranded DNA, all prepared in (1) of Example 2, were used as substrate DNAs.

To the reaction solution used in (3) of Example 2, an annealed substrate DNA and Pfu-HJC endonuclease obtained in (3) of Example 3 were each added at the final concentration of 10 nM to conduct the reaction as in (3) of Example 2.

To 8 μl of the reaction solution, 6 μl of loading buffer for sequencing [98% formamide, 10 mM trisodium ethylenediaminetetraacetate, 0.025% xylene cyanol, 0.025% bromophenol blue] was added, heat-treated at 95° C. for 2 minutes, and then a 2.5 μl aliquot was electrophoresed on a denaturing polyacrylamide gel containing 8 M urea. After drying, the acrylamide gel was subjected to autoradiography to determine the presence or absence of cleavage bands. In result, strong substrate specificity was observed for the four-way junction structure of which center migrates and the four-way junction structure of which center does not migrate, and it was found that the three-way junction structure of which center migrates and the three-way junction structure of which center does not migrate were also slightly cleaved (FIG. 7). It was confirmed that the loop-out structure was also cleaved, though at a still lower efficiency.

(2) Determination of the Sites of Cleavage

In order to determine the sites of cleavage in the substrate DNAs by HJC endonuclease of the present invention, the four-way junction structure of which center migrates, the four-way junction structure of which center does not migrate, the three-way junction structure of which center migrates, the three-way junction structure of which center does not migrate, and the loop-out structure, wherein each arm was end-labeled, prepared in (1) of Example 2 were used in the reactions, and detected as in (1) of Example 4. As markers, a GA ladder was prepared from the same end-labeled primers by the Maxam-Gilbert method, and electrophoresed on the adjacent lane to determine the sites of cleavage by comparing the sizes of the both bands.

In result, as indicated by arrowheads in FIGS. 1–5, a pair of sites primarily (more than 90%) cleaved was determined for each substrate, although cleavage was observed at more than one sites.

(3) Determination of the Cleavage Pattern

In order to determine the cleavage pattern of Pfu-HJC endonuclease of the present invention, the four-way junction structure prepared in (1) of Example 2, in which structure the labeled arm was short, was used as a substrate DNA to conduct a reaction as in (1) of Example 4. After stopping the reaction, DNAs were recovered by ethanol precipitation, and the DNAs recovered were used in a ligation reaction with T4 DNA ligase. After completion of the reaction, bands were detected as in (1) of Example 4. As markers, end-labeled 70-mer and 59-mer primers were electrophoresed on the adjacent lane to determine whether the cleaved sites were ligated by the ligation reaction (whether the 70-mer band was generated) by comparing the sizes of both bands.

In result, as shown in FIG. 8, a band was observed at the position of 70-mer, which was generated by re-ligation of the DNA strand cleaved by Pfu-HJC endonuclease with DNA ligase.

Example 5

(1) Amino Acid Sequence Homology Search

Regarding the structure of Pfu-HJC, proteins exhibiting significant homologies to the amino acid sequence predicted from the base sequence of DNA encoding the ORF obtained in (1) of Example 3 were searched through known DNA and protein databases, using BRAST search available on the Internet at the home page of National Center for Biotechnology Information. In result, as shown in FIG. 9, genes that may encode homologous sequences were found in four kinds of archaebacteria of which entire genomic sequences have been decoded. These genes have been registered as having unknown functions, and there existed no other proteins or open reading frames exhibiting high homologies regardless of whether functions have been known or unknown. Thus, to date, there have been no findings regarding proteins having sequences similar to that of Pfu-HJC endonuclease of the present invention.

Example 6

(1) Thermostability

In order to determine the thermostability of Pfu-HJC endonuclease of the present invention, Pfu-HJC endonuclease obtained in (3) of Example 3 was subjected to heat treatments at 80, 90, and 95° C. for 10, 30, and 60 minutes. An overnight heat treatment at 90° C. (about 16 hours) was also conducted. Heat-treated Pfu-HJC endonuclease was added to attain 10 nM, and the reaction and electrophoresis were conducted as in (3) of Example 2 to detect cleavage bands (FIG. 10). In result, it was found that Pfu-HJC endonuclease retained its activity of cleaving four-way junction structure DNAs even after heat treatment at 95° C. for 60 minutes or at 90° C. for about 16 hours.

---

What is claimed is:

1. An isolated protein which (a) is thermostable and retains its deoxyribonuclease activity at least even after incubation at 80° for 10 minutes, (b) is derived from Archaebacteria and (c) has a deoxyribonuclease activity of specifically cleaving a Holliday structured DNA into two sets of double-stranded DNAs, said Holliday structured DNA being an intermediate structure in a DNA recombination process.

2. The isolated protein according to claim 1, which retains its deoxyribonuclease activity at least even after incubation at 95° C. for one hour or at 90° C. for 16 hours.

3. The isolated protein according to claim 2, which comprises a) the amino acid sequence of SEQ ID NO: 1 or b) the amino acid sequence of SEQ ID NO: 1 wherein one to several amino acids in the sequence are deleted, substituted, or added.

4. The isolated protein according to claim 1, which comprises a) the amino acid sequence of SEQ ID NO: 1 or b) the amino acid sequence of SEQ ID NO: 1 wherein one to several amino acids in the sequence are deleted, substituted, or added.

* * * * *